(12) United States Patent
Gunes et al.

(10) Patent No.: US 10,765,125 B2
(45) Date of Patent: Sep. 8, 2020

(54) LIPID BASED FOAM

(71) Applicant: NESTEC S.A., Vevey (CH)

(72) Inventors: Zeynel Deniz Gunes, Lausanne (CH); Olivier Schafer, Epalinges (CH); Helen Chisholm, Cheseaux (CH); Helene Deyber, Jougne (FR); Cindy Pelloux, Thonon-les-bains (FR); Bernard Paul Binks, East Yorkshire (GB)

(73) Assignee: Societe des Produits Nestle S.A., Vevey (CH)

( * ) Notice: Subject to any disclaimer, the term of this patent is extended or adjusted under 35 U.S.C. 154(b) by 130 days.

(21) Appl. No.: 15/559,982

(22) PCT Filed: Mar. 22, 2016

(86) PCT No.: PCT/EP2016/056290
§ 371 (c)(1),
(2) Date: Sep. 20, 2017

(87) PCT Pub. No.: WO2016/150978
PCT Pub. Date: Sep. 29, 2016

(65) Prior Publication Data
US 2018/0070598 A1    Mar. 15, 2018

(30) Foreign Application Priority Data

Mar. 23, 2015   (EP) .................................... 15160345

(51) Int. Cl.
*A23D 9/04* (2006.01)
*A23L 33/20* (2016.01)
(Continued)

(52) U.S. Cl.
CPC ............... *A23D 9/04* (2013.01); *A21D 2/165* (2013.01); *A21D 13/068* (2013.01); *A23D 7/05* (2013.01);
(Continued)

(58) Field of Classification Search
None
See application file for complete search history.

(56) References Cited

U.S. PATENT DOCUMENTS 3,253,928 A    5/1966    Bedenk et al.
3,549,387 A    12/1970   Howard
(Continued)

FOREIGN PATENT DOCUMENTS

DE    102012021545 A1    4/2014
WO    2016150977 A1     9/2016

OTHER PUBLICATIONS

Roquette, "Neosorb P 100 T", file:///C:/Users/egwartney/Downloads/roquette_quality_specification-sheet_neosorb-p-100-t_10_423141_en.pdf, Apr. 2019, downloaded Aug. 21, 2019. (Year: 2019).*
(Continued)

*Primary Examiner* — Elizabeth Gwartney
(74) *Attorney, Agent, or Firm* — K&L Gates LLP

(57) ABSTRACT

The present invention relates generally to the field of foams. One aspect of the invention provides a foam having a continuous lipid phase and a porosity of between and 80% wherein, at a temperature at which the lipid phase has a solid lipid content between 0.1 and 80% the foam comprises gas bubbles having at least 50% of their surface occupied by crystals comprising triglycerides. Further aspects of the invention are a product comprising a foam and a process for forming a foam.

13 Claims, 5 Drawing Sheets

(51) Int. Cl.
  *A21D 2/16*    (2006.01)
  *A23G 1/52*    (2006.01)
  *A61K 8/04*    (2006.01)
  *A61K 8/92*    (2006.01)
  *A61Q 19/00*   (2006.01)
  *A23D 7/05*    (2006.01)
  *A21D 13/068*  (2017.01)

(52) U.S. Cl.
  CPC ................ *A23G 1/52* (2013.01); *A23L 33/20* (2016.08); *A61K 8/046* (2013.01); *A61K 8/922* (2013.01); *A61Q 19/00* (2013.01)

(56) References Cited

U.S. PATENT DOCUMENTS

| | | | |
|---|---|---|---|
| 3,637,402 A * | 1/1972 | Reid | ........................ A23D 9/02 426/417 |
| 2009/0246345 A1 | 10/2009 | Ichiyama et al. | |
| 2010/0189867 A1 | 7/2010 | Blijdenstein et al. | |

OTHER PUBLICATIONS

Heertje et al. "Liquid Crystalline Phases in the Structuring of Food Products" Lebensim-Wiss. u.-Technol., 1998, vol. 31, pp. 387-396.
European Office Action Appl No. 16 714 313.0 dated Nov. 20, 2019.

* cited by examiner

LIPID BASED FOAM

CROSS REFERENCE TO RELATED APPLICATIONS

The present application is a National Stage of International Application No. PCT/EP2016/056290, filed on Mar. 22, 2016, which claims priority to European Patent Application No. 15160345.3, filed on Mar. 23, 2015, the entire contents of which are being incorporated herein by reference.

FIELD OF THE INVENTION

The present invention relates generally to the field of foams. One aspect of the invention provides a foam having a continuous lipid phase and a porosity of between 1 and 80% wherein, at a temperature at which the lipid phase has a solid lipid content between 0.1 and 80% the foam comprises gas bubbles having at least 50% of their surface occupied by crystals comprising triglycerides. Further aspects of the invention are a product comprising a foam and a process for forming a foam.

BACKGROUND OF THE INVENTION

Lipid foams are of particular interest to the consumer products industry, having the potential to provide new textures and sensory properties for food and nutrition products as well as in cosmetic products. In food products there is increasing concern about the amount of fat consumed in people's diet. Foaming lipids provides a method to maintain product volume whilst reducing the fat content.

The major difficulty in generating stable foam structures within lipid-based systems as compared to water-based systems lies in the lack of suitable surfactants for forming stable interfaces between air and lipid. Those surfactants which have been proposed may not be suitable for stabilizing edible foams due to toxicity or unpleasant taste. As a consequence, the most common approach for obtaining stable foams in a lipid-based matrix is by forming a rigid network in the bulk material, for example by forming a rigid network of crystals in a liquid lipid continuous phase or by rapidly cooling the lipid so as to solidify the bulk material. As well as affecting the texture in a way which may not always be desired, both of these approaches lead to constraints when processing the foam. Having a rigid network in the liquid lipid continuous phase affects the ability of the foam to be pumped, deposited, or mixed with other components without destroying the stabilizing network leading to coalescence of bubbles. A foam stabilized by solidifying the bulk is generally unstable before solidification and so can only be maintained as a foam for a short period and cannot be subject to substantial shear forces during processing.

Hence, there is a need in the industry to find better solutions to produce stable lipid foams, in particular edible lipid foams which taste good and are made from natural ingredients. An object of the present invention is to improve the state of the art and to provide an improved solution to overcome at least some of the inconveniences described above or at least to provide a useful alternative. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to". The object of the present invention is achieved by the subject matter of the independent claims. The dependent claims further develop the idea of the present invention.

SUMMARY OF THE INVENTION

Accordingly, the present invention provides in a first aspect a foam having a continuous lipid phase and a porosity of between 1 and 80% wherein, at a temperature at which the lipid phase has a solid lipid content between 0.1 and 80%, the foam comprises gas bubbles having at least 50% of their surface occupied by crystals comprising triglycerides. In a second aspect, the invention relates to a product comprising the foam of the invention. A third aspect of the invention relates to a process for forming a foam, the process comprising the steps of providing a composition comprising triglycerides and having a lipid content greater than 20 wt. %; controlling the temperature of the composition such that the composition comprises triglyceride crystals, has a solid lipid content between 0.1 and 80% and forms a gel; and aerating the gel to form a foam.

It has been surprisingly found by the inventors that, by cooling a liquid lipid composition comprising triglycerides to a temperature at which there is partial crystallization and a gel is formed and then whipping the composition, a stable foam is produced. The gas bubbles in the foam were found to be coated in triglyceride crystals. By using a process of prolonged and intensive whipping, very stable assemblies of crystal-wrapped bubbles can be obtained. The crystals jam together around the bubble, leading to mechanical stability and resisting bubble shrinkage. The bulk remains soft, e.g. there is no rigid network of crystals in between the bubbles. The foam can be diluted with additional oil and still remain stable (unless so much oil is added that it dissolves the crystals). The foam may be further cooled such that the continuous phase solidifies, but if the foam is re-heated and the continuous phase re-melts, the stable crystal-wrapped bubbles remain until the temperature is raised to the point where all crystals melt (or substantially all crystals melt). The foams according to the invention do not easily destabilize under mechanical processing, unlike many particle-stabilized foams or conventional surfactant stabilized foams.

DETAILED DESCRIPTION OF THE INVENTION

Figure 1:
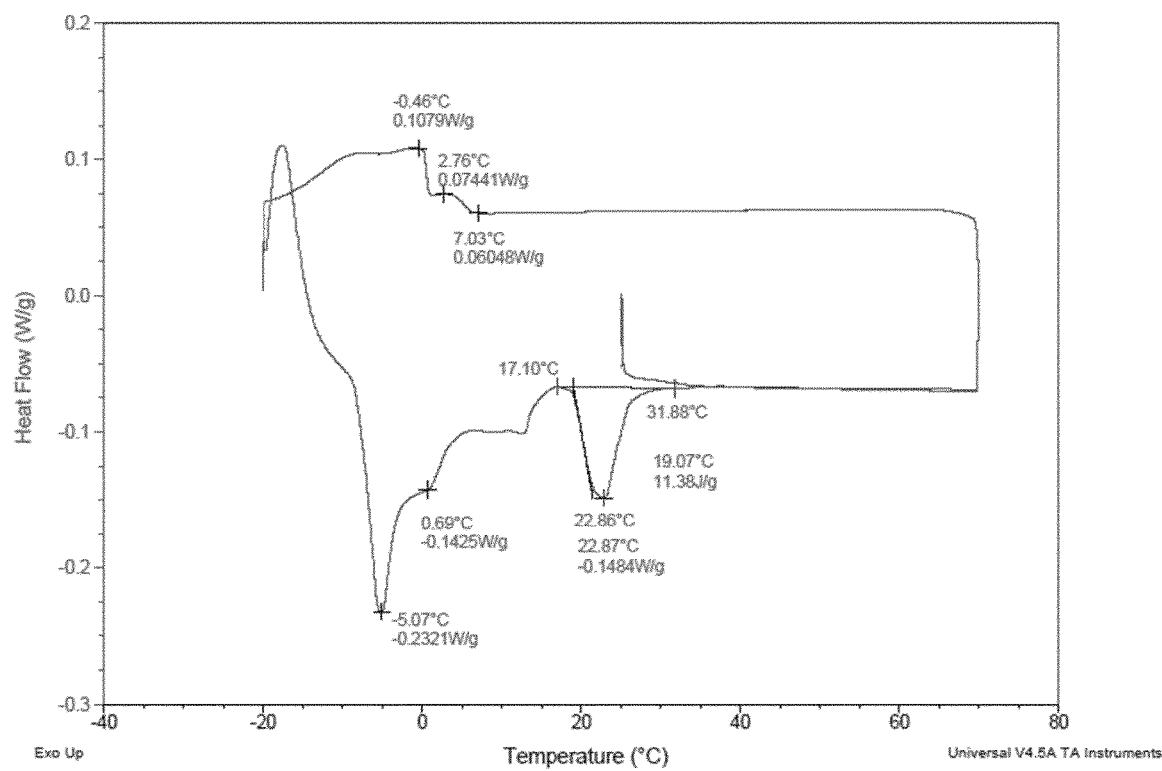
FIG. 1 shows a differential scanning calorimeter crystallization and melting trace for 20 wt. % cocoa butter in high oleic sunflower oil.

Consequently the present invention relates in part to a foam having a continuous lipid phase and a porosity of between 1 and 80%, for example between 10 and 75%, wherein, at a temperature at which the lipid phase has a solid lipid content between 0.1 and 80%, for example between 0.1 and 60%, for example between 0.5 and 40%, for example between 1 and 20%, for example between 5 and 20%, the foam comprises gas bubbles having at least 50% of their surface occupied by crystals comprising triglycerides. A foam is a dispersion of a gas in a solid or liquid medium. The gas may be any gas commonly used for foam generation such as $CO_2$, $N_2$ or $N_2O$, but typically the gas is air. The term porosity refers to the fraction of the volume of gas-filled voids over the total volume, as a percentage between 0 and 100%. The lipid phase of the foam may comprise lipidic solids, semisolids or liquids. The lipid phase of the foam may comprise water-insoluble esters of glycerol with fatty acids.

Triglycerides, also called triacylglycerols or triacylglycerides, are esters derived from glycerol and three fatty acids. The temperature at which the lipid phase has a solid lipid content between 0.1 and 80% may be measured by any methods well known in the art. For example the solid lipid content at different temperatures may be measured by pulsed NMR, for example according to the IUPAC Method 2.150. The solid lipid content at different temperatures may also be measured by differential scanning calorimetry. The result of a measurement of solid lipid content is commonly referred to as the solid fat content. Although it is possible to obtain solid lipid contents intermediate between 0 and 100% with a pure triglyceride composition by exploiting the kinetics of crystallization and heat transfer, in general it is preferable that the lipid phase comprises a mixture of different triglycerides with different melting points. Indeed, pure triglycerides are expensive and so are not preferred. All components of the foam may be edible. The term "edible" refers to substances which can be eaten safely. Whilst the current invention is not limited to substances permitted for consumption in any particular jurisdiction, edible compositions may for example comprise materials approved for human consumption by the U.S. Food and Drug Administration.

The foam of the invention may have a low moisture content, for example the foam may contain less than 5% water by weight, for example less than 2.5% water by weight. It should be noted that the foam of the present invention can be formed without moisture, for example without the use of surfactants in water or the formation of an emulsion containing water. Food ingredients that are completely free from moisture are rare, but the foam of the invention may be essentially free from water.

The percentage of the gas bubbles' surface occupied by crystals may be measured using microscopy (for example optical and/or confocal microscopy), coupled with suitable image analysis techniques. With a high level of surface coverage it may be immediately obvious after inspection by microscopy that at least 50% of the surface of the gas bubbles is occupied by crystals.

The crystals occupying at least 50% of the surface of the gas bubbles jam together, resisting any shrinkage of the bubbles and providing a stable, flowable foam when the continuous phase is fluid, such as when the lipid phase has a solid lipid content between 0.1 and 80%. The crystals occupying at least 50% of the surface of the gas bubbles may cause the bubbles to have a non-relaxing shape when the foams are diluted with oil. In the context of the present invention the term flowable foam refers to a foam which can be processed in pumping or stirring units using typical food process equipment without undergoing obvious structural coarsening or collapse. The flowable foam may be flowable under gravity after stirring (for example at 20° C.).

The fat-based confectionery material may comprise gas bubbles having their surface occupied by triglycerides, for example triglyceride crystals, such that their surface density is at least 15 mg·m$^{-2}$, for example at least at least 25 mg·m$^{-2}$, for example at least 50 mg·m$^{-2}$, for further example at least at least 200 mg·m$^{-2}$. The surface density of triglycerides at the surface may be measured by diluting foams by oil addition and gentle manual stirring. The samples are then left to at rest until phase separation occurred between an upper layer formed by bubble accumulation, due to buoyancy mismatch between air and the continuous oil phase, and a bottom phase formed by oil and the remaining non-adsorbed triglyceride crystals. The upper foam layers are then carefully removed and the subnatants are collected for analysis. The concentration of triglycerides can be determined by gas-chromatography. From the initial concentration of triglycerides in the material before whipping (the gel) and the measured concentration in the supernatant, the interfacial area can be calculated:

Interfacial area (S) developed by a foam:

$$S = \frac{6\phi V}{D}$$

V: volume of foam (m$^3$)

φ: porosity

D: bubble Sauter diameter (m) as measured by optical microscopy/tomography

OR/porosity: The levels of aeration may be estimated by Over-Run (OR) or porosity (φ) measurements in standardized plastic cups.

$$\% \, OR = \frac{m_{non\,aerated} - m_{aerated}}{m_{aerated}} \times 100$$

$$\% \, \phi = \frac{OR}{OR + 100} \times 100$$

Concentration of adsorbed triglycerides at interface:

$$C_{ads} = C_{ini} - C_{non\text{-}ads} \times X$$

$C_{ads}$: glyceride concentration, relative to the oil phase, adsorbed at the air-oil interface of the bubbles $C_{ini}$: initial concentration of glyceride in the gel $C_{non-ads}$: non-adsorbed glyceride concentration as titrated from the diluted subnatant X: dilution factor applied to the foam before collecting the subnatant Adsorption surface density:

$$\Gamma = \frac{c_{ads}(1-\phi)V}{S}$$

The foam of the invention has a number of advantages. At temperatures where the continuous phase is fluid the foam's stability makes it easy to process without damaging the foam. The composition of the foam may be adjusted so that there is a high proportion of liquid lipid at the temperature at which the foam is used, and this allows for soft textures while maintaining good stability. The inventors were surprised to find that the foam remains stable (at rest and during processing) when combined with other materials, for example other food materials such as proteins, emulsifiers and solid particles.

The foam may be cooled such that the continuous lipid phase is no longer fluid. However, a characteristic of the foam is that, at a temperature at which the lipid phase has a solid lipid content between 0.1 and 80%, for example after re-heating, the foam still comprises gas bubbles having at least 50% of their surface occupied by crystals comprising triglycerides. This is in contrast to foams which are simply stabilized by crystallizing the bulk. A high proportion of the lipid crystals in the foam of the invention occupy the surface of the gas bubbles at a temperature at which the lipid phase has a solid lipid content between 0.1 and 80%. For example, at least 50% by volume of the bubbles may have at least 50% of their surface occupied by crystals comprising triglycerides. The lipid phase may comprise fats such as coconut oil, palm kernel oil, palm oil, cocoa butter, butter oil, lard, tallow, oil/fat fractions such as lauric or stearic fractions, hydrogenated oils, and blends thereof as well as sunflower oil, rapeseed oil, olive oil, soybean oil, fish oil, linseed oil, safflower oil, corn oil, algae oil, cottonseed oil, grape seed oil, nut oils such as hazelnut oil, walnut oil, rice bran oil, sesame oil, peanut oil, palm oil, palm kernel oil, coconut oil, and emerging seed oil crops such as high oleic sunflower oil, high oleic rapeseed, high oleic palm, high oleic soybean oils & high stearin sunflower or combinations thereof. For example, the lipid phase may comprise fats selected from the group consisting of cocoa butter, shea butter, illipe butter, sal fat, kokum butter, mango kernel fat, palm oil, coconut oil, soybean oil, rapeseed oil, cottonseed oil, sunflower oil, safflower oil, olive oil and hydrogenation products, interesterification products, fractions and combinations of these.

It is advantageous that the foam is stabilized by triglyceride crystals as these have good consumer acceptance, for example in food products. At a temperature at which the lipid phase has a solid lipid content between 0.1 and 80%, the foam may comprises gas bubbles having at least 50% of their surface occupied by triglyceride crystals. The lipid phase may comprise at least 60 wt. % triglycerides, for example at least 75 wt. % triglycerides, for example at least 90 wt. % triglycerides.

It is beneficial to be able to stabilize a foam having a continuous lipid phase without needing to use triglycerides with high chain length fatty acids. Such high chain length fatty acids, especially saturated ones, affect the organoleptic properties of the foam, giving a heavy and waxy mouthfeel. The inventors were surprised to find that foams according to the invention could be effectively stabilized without using triglycerides with high chain length fatty acids, for example by using the process of the invention. The gas bubbles comprised within the foam of the invention may have their surface occupied by triglycerides all of whose fatty acids have a carbon chain length less than 22. The gas bubbles comprised within the foam of the invention may have their surface occupied by triglycerides all of which have an average fatty acid chain length less than 20. For example, the triglyceride palmitic-oleic-stearic (POSt) has an average chain length of 17.3 as palmitic acid is C16, oleic acid is C18 and stearic acid is C18.

The foam of the invention may contain more than 95% by weight of total lipids (for example more than 98%, for further example more than 99%) of triglycerides all of whose fatty acids have a carbon chain length less than 22. The foam of the invention may contain more than 95% by weight of total lipids (for example more than 98%, for further example more than 99%) of triglycerides all of whose fatty acids have an average chain length less than 20.

The crystallization behaviour of the lipid phase may be examined using differential scanning calorimetry (DSC), a technique in which the difference in the amount of heat required to increase the temperature of a sample and reference is measured as a function of temperature. For example, a sample comprising the lipid phase may be heated to completely melt all the lipid, cooled to record the crystallization signature and then reheated to record the melting signature. When the cooling protocol brings the mixture so low in temperature that the system solidifies in bulk then the lipid phase in the foam of the current invention may show at least two distinct endothermic melting "peaks" during the reheating phase, the at least two endothermic melting "peaks" being separated by at least 10° C., for example at least 15° C., for example at least 20° C. The area under each of the at least two peaks may be at least 10% of the area under all peaks in the melting trace. Depending on the DSC equipment used, endothermic heat flows may be shown as positive or negative peaks.

The inventors have found that good results may be obtained using a fat or blend of fats having a broad range of crystallization temperatures. Such fats or blends of fats have broad ranges of crystallization peaks when measured in a differential scanning calorimeter (DSC). These broad ranges of crystallization temperatures allow flexibility in selecting a temperature at which the lipid phase has a solid lipid content between 0.1 and 80% (for example between 0.1 and 60%, for example between 0.5 and 40%, for example between 1 and 20%, for example between 5 and 20%) before aerating the composition to form a foam. DSC measurements of fats are conveniently carried out between 80° C. and −20° C. The lipid phase in the foam of the invention may have at least 80% of its total crystallization enthalpy between 80° C. and −20° C. occurring in a temperature range of at least 20° C., for example a range of at least 30° C. The lipid phase in the foam of the invention may have at least 50% of its total crystallization enthalpy between 80° C. and −20° C. occurring in a temperature range between 40° C. and 15° C., for example at least 80% of its total crystallization enthalpy between 80° C. and −20° C. occurring in a temperature range between 40° C. and 15° C. The lipid phase in the foam of the invention may have at least 50% of its total crystallization enthalpy between 80° C. and −20° C. occurring in a temperature range between 20° C. and −5° C., for example at least 80% of its total crystallization enthalpy between 80° C. and −20° C. occurring in a temperature range between 20° C. and −5° C. Crystallization enthalpy measurements may for example be measured by DSC.

The crystals comprising triglycerides occupying the surface of the gas bubbles in the foam according to the invention may form layers having an average thickness below 5 μm, for example between 0.2 and 5 μm. The lipid crystals comprising triglycerides occupying the surface of the gas bubbles in the foam according to the invention may form layers having an average thickness below 2 μm, for example between 0.2 and 2 μm. The lipid crystals comprising triglycerides occupying the surface of the gas bubbles in the foam according to the invention may form layers having an average thickness between 0.01 μm and 5 μm, for example between 0.05 μm and 2 μm, for further example between 0.2 μm and 1 μm. Thin layers of crystals provide an advantage as a smaller amount of crystals are required to wrap the bubbles and hence a smaller amount of higher melting components. As the bubble size in a foam decreases, for the same volume of gas in the foam overall the surface area of the bubbles increases, and so more crystals would be needed to coat the bubbles. As the invention provides gas bubbles coated with thin layers of crystals, foams with low densities can be formed with a small bubble size, providing interesting and attractive textures.

The foam of the invention does not rely on a rigid network in the continuous phase for its stability. This means that, at temperatures where a high proportion of the lipid phase is liquid, the foam is stable yet can be soft and flowable. Accordingly, the foam of the invention may have no rigid network in the continuous lipid phase at a temperature at which the lipid phase has a solid lipid content between 0.1 and 80%. For example the foam, at a temperature at which the lipid phase has a solid lipid content between 0.1 and 80% (for example between 0.1 and 60%, for example between 0.5 and 40%, for example between 1 and 20%, for example between 5 and 20%), may flow under gravity without losing more than 10% of its porosity (for example without losing more than 5% of its porosity). A rigid network is present when flow induces partial instability of the structure. On applying shear to a rigid network, a solid type of initial flow is observed. For example if a system having a rigid network is sheared in a rheometer, an initial resistance of elastic (or rigid) type would be observed, followed by a transition through maximal resistance (breakage of the rigid structure) before the structure would recover to being flowable (at least in part). The transition is then not rapidly reversible (no rapid recovery of the rigid network e.g. within a few seconds or minutes). This is in contrast to the behaviour of foams having no rigid network.

Most lipid materials used commercially are mixtures of different molecules. Vegetable and animal fats for example contain a range of different triglycerides. As a consequence, when cooling these fats, a fraction of the triglycerides will start to crystallize while the rest of the fat remains liquid. The inventors have found that by cooling liquid fats so that part of the triglycerides crystallize and a gel forms, and then aerating the gel, a stable foam may be produced. The gel structure may continue to develop during and after foaming. The inventors found for example that on cooling olive oil (80% refined, 20% extra virgin) to −23° C. a gel forms. After re-warming the gel by leaving at 5° C. for 3 hours, whipping the gel creates a stable foam (overrun around 65%) with gas bubbles having their surface occupied by triglyceride crystals. For ease of processing, the temperature may be raised before whipping, as long as some crystals and the gel remain. For example the inventors were able to whip the olive oil gel at 5° C., after solidifying it by cooling it to e.g. −10° C. and leaving it at −10° C. for a few hours, then leaving to partially melt at 5° C. before whipping. In such a foam, no additional stabilizer material needs to be added to the liquid fat to enable a foam to be formed. Accordingly, in one embodiment of the invention, the lipid phase comprises one or more fats and the crystals comprising triglycerides occupying the surface of the gas bubbles comprise triglycerides from all the one or more fats. The fats may be vegetable fats. The fats may be selected from the group consisting of cocoa butter, olive oil, high stearic sunflower oil and combinations of these. The composition of triglycerides occupying surface of the gas bubbles may be richer in higher melting triglycerides than the bulk fat. In the context of the current invention the terms oils and fats are used interchangeably. Conventionally in industry, the term oils is used for fats which are liquid at the temperature at which they are traditionally sold. In another embodiment of the invention, one or more higher melting-point fats may be included in the lipid phase of the foam to promote the formation of crystals to occupy the surface of the gas bubbles when the majority of the lipid phase is still liquid. The invention may provide a foam wherein the lipid phase comprises one or more higher melting-point (HMP) fats and one or more lower melting-point (LMP) fats and wherein the melting-point of the lowest melting higher melting-point fat is at least 10° C., for example at least 15° C., for example at least 20° C., above that of the melting point of the highest melting lower melting-point fat and wherein the lower melting-point fats are present at a level of greater than 50 wt. % of the total lipid in the lipid phase, for example greater than 60 wt. %, for example greater than 70 wt. %, for example greater than 90 wt. %. A lipid phase composition as described facilitates the formation and stability of the foam, with crystals from the higher melting-point fats occupying the gas bubble surfaces while the lower melting-point fats maintain a fluid continuous phase to enable aeration, for example by whipping.

Consider a lipid phase which consists of 6 wt. % high melting palm oil fraction (mpt. 63° C.), 40 wt. % cocoa butter (mpt. 35° C.) and 54 wt. % high oleic sunflower oil (mpt. −17° C.). The lipid phase has two HMP fats (high melting palm oil fraction and cocoa butter) and one LMP fat (high oleic sunflower oil). The melting point of the lowest melting HMP fat (cocoa butter) is 35° C., which is at least 10° C. above that of the melting point of the highest melting LMP fat, i.e. high oleic sunflower oil with a melting point of −17° C. The LMP fat (HOSFO) is present at 54 wt. % of the total lipid.

For different product applications and usage temperatures, the melting points of the fats in the lipid phase may vary. The melting-point of the lowest melting HMP fat may be above 10° C., for example above 20° C., for example above 30° C., for example above 40° C. A combination of a small quantity of high melting fat with a large amount of low melting fat can provide a stable foam at room temperature and below, which is particularly beneficial for edible foams as they achieve stability without causing excessive waxiness in the mouth, and without an unwanted increase in saturated fat content. For example, the melting-point of the lowest melting HMP fat may be above 40° C., for example between 40 and 90° C., and the lower melting-point fats may be present at a level of greater than 90 wt. %. For example, the melting-point of the lowest melting HMP fat may be above 30° C., for example between 30 and 50° C., and the lower melting-point fats may be present at a level of greater than 75 wt. %. The crystals occupying the surface of the gas bubbles may comprise triglycerides from the HMP fats. Fats present in minor quantities with melting-points between the temperature of the lowest melting HMP fat and the highest melting LMP fats do not significantly affect the efficiency of foam formation. The melting-point of the lowest melting higher melting-point fat may be at least 10° C., for example at least 15° C., for example at least 20° C., above that of the melting point of the highest melting lower melting-point fat when fats present at levels below 1 wt. % of the lipid content of the lipid phase are discounted. The melting-point of a fat may for example be the temperature at which it has a 1% solid fat content as measured by pulsed NMR.

The one or more higher melting-point fats in the foam of the invention may be selected from the group consisting of cocoa butter, shea butter, kokum butter, illipe butter, sal fat, mango kernel fat, palm kernel oil, palm oil, coconut oil, milk fat, high stearic sunflower oil and hydrogenation products, inter-esterification products, fractions and combinations of these; and the one or more lower melting-point fats may be selected from the group comprising sunflower oil (high oleic and standard), coconut oil, safflower oil, rapeseed oil, olive oil and combinations and fractions of these. The one or more higher melting-point fats in the foam of the invention may have a melting point above 20° C. and the one or more lower melting-point fats in the foam of the invention may have a melting point below 20° C.

The higher melting-point fats in the foam of the invention may comprise cocoa butter, for example inter-esterified cocoa butter, and the lower melting-point fats in the foam of the invention may comprise sunflower oil, for example high oleic sunflower oil. The higher melting-point fats in the foam of the invention may comprise a high melting fraction of palm oil, and the lower melting-point fats in the foam of the invention may comprise sunflower oil, for example high oleic sunflower oil. The higher melting-point fats in the foam of the invention may comprise hydrogenated coconut oil and the lower melting-point fats in the foam of the invention may comprise sunflower oil, for example high oleic sunflower oil. The higher melting-point fats in the foam of the invention may comprise hydrogenated palm kernel oil and the lower melting-point fats in the foam of the invention may comprise sunflower oil, for example high oleic sunflower oil. The higher melting-point fats in the foam of the invention may comprise shea butter, for example fractionated or interesterified shea butter, and the lower melting-point fats in the foam of the invention may comprise sunflower oil, for example high oleic sunflower oil. The higher melting-point fats in the foam of the invention may comprise illipe butter, for example fractionated or interesterified illipe butter, and the lower melting-point fats in the foam of the invention may comprise sunflower oil, for example high oleic sunflower oil. The higher melting-point fats in the foam of the invention may comprise high stearic sunflower oil stearin, and the lower melting-point fats in the foam of the invention may comprise high oleic sunflower oil.

Typically, lower melting fats have lower levels of saturated fatty acids than higher melting fats. Consumption of saturated fatty acids have been linked to increased levels of LDL cholesterol in the blood and heart diseases and so it would be advantageous to be able to reduce the consumption of saturated fatty acids. By being able to create a foam from a lipid phase with a high percentage of lower melting fats the invention provides a means to reduce the saturated fatty acid content of edible foams. The foam of the invention may be low in saturated fatty acids, for example the foam of the invention may have a saturated fatty acid content of less than 45 wt. % of the total fatty acid content, for example less than 35 wt. % of the total fatty acid content, for example less than 25 wt. % of the total fatty acid content. The foam of the invention provides an equivalent volume for less weight of material and hence reduces the total fat and therefore the saturated fatty acid content of any food product comprising it.

The inventors have found that the addition of particles may aid the foam stability, reducing coarsening over time and providing better foam homogeneity. Solid particles having a particle size of less than 500 µm may be dispersed in the foam. Particle size may be measured by the methods known in the art consistent with the size being measured. For example, a particle size less than 500 µm may be confirmed by passage through a standard US sieve mesh 35. The solid particles dispersed in the foam may have a particle size less than 180 µm (e.g. measured by passage through US mesh 80). The solid particles dispersed in the foam may have a D90 particle size measured by laser light scattering of less than 100 µm, for example less than 50 µm, for example less than 30 µm. The solid particles dispersed in the foam may be selected from the group consisting of modified starch, maltodextrin, inorganic salt (for example edible inorganic salt), protein particles, fibres (for example slowly digestible or digestion resistant carbohydrates), plant particles (for example cocoa particles, coffee particles, spices or herbs), sugars (for example sucrose), hydrogel particles and combinations of these. The solid particles dispersed in the foam may be maltodextrin. The solid particles may be present at a level of between 1 and 500% of the total lipid weight in the foam, for example between 1 and 200% of the total lipid weight in the foam, for example between 1 and 100% of the total lipid weight in the foam, for example between 1 and 20% of the total lipid weight in the foam, for further example between 5 and 20% of the total lipid weight in the foam.

The foam of the invention may be comprised within a food product or cosmetic product. For example the foam of the invention may be a food product; for example an aerated dressing or sauce (sweet or savoury); an aerated dairy product such as a mousse dessert; an aerated beverage or beverage enhancer; or an aerated nutritional formula (for example a nutritional formula for dysphagia patients which is easier to swallow). Incorporating a gas such as air into a food product can be used to create an attractive texture and also provides a means to reduce the fat content of a food without reducing its volume. The foam may be generated at the point-of-sale, for example to provide a topping for a beverage or ice cream. The foam of the invention may be a cosmetic product, for example a foamed massage oil (such as foamed baby oil) or an aerated skincare cream. The foam of the invention may be comprised within a pet food or a bakery product (such as added to a bakery dough for example as an aerated biscuit shortening).

In a further aspect, the invention provides a process for forming a foam, the process comprising the steps of providing a composition comprising triglycerides and having a lipid content greater than 20 wt. % (for example greater than 30 wt. %, for example greater than 40 wt. %, for example greater than 50 wt. %, for example greater than 60 wt. %); controlling the temperature of the composition such that the composition comprises triglyceride crystals, has a solid lipid content between 0.1 and 80% (for example between 0.1 and 60%, for example between 0.5 and 40%, for example between 1 and 20%, for example between 5 and 20%), and forms a gel; and aerating the gel to form a foam. The foam may comprise gas bubbles having their surface occupied by crystals comprising triglycerides. In the context of the present invention the term aerating refers to foaming by the incorporation of gas bubbles, the gas not necessarily being air. Aeration may be achieved by any of the techniques known in industry, for example mechanical agitation, passive mixing (e.g. passing through slit or nozzle), pressure drop (e.g. to vacuum, or from elevated pressure to atmospheric pressure) or sparging (when a chemically inert gas is bubbled through a liquid).

A gel is a non-fluid network characterised by a continuous liquid throughout its whole volume. The gel of the process of the invention may have a continuous lipid phase. The gel of the process of the invention may have a gel property arising from a crystal network, for example a network of crystals of average size below 100 microns throughout the matrix. The gel of the process of the invention may have between 3 and 30% of the total lipid by weight in the form of crystals, for example between 5 and 20%. A gel may be defined by its rheology. For example at a frequency of 1 Hz, the measured linear shear elastic modulus G' of a gel may be greater than 10 Pa and the viscous modulus G" may be less than G'. Gels most suitable for foam generation have a linear shear elastic modulus G' initially in the range $10^2$-$10^7$ Pa at 1 Hz, for example a linear shear elastic modulus G' initially in the range $10^2$-$10^6$ Pa at 1 Hz, for further example a linear shear elastic modulus G' initially in the range $10^3$-$10^6$ Pa at 1 Hz.

The composition comprising triglycerides may comprise a range of different triglycerides with different melting points. The crystallization behaviour of the composition comprising triglycerides may be examined using differential scanning calorimetry (DSC). Aeration may be performed at a temperature below the highest melting peak maximum, the temperature being such that the solid lipid content is between 0.1 and 80%, preferably at a temperature below the whole peak area of the highest endothermic melting peak. For example, in a mixture of 20% cocoa butter in high oleic sunflower oil, the highest melting peak was found to have a maximum at 23° C. Good results were obtained by aerating the mixture which had been recently cooled to a temperature of 17° C., the solid lipid content being between 0.1 and 80%.

The composition comprising triglycerides in the process of the invention may comprise one or more higher melting-point (HMP) fats and one or more lower melting-point (LMP) fats wherein the melting-point of the lowest melting higher melting-point fat is at least 10° C., for example at least 15° C., for example at least 20° C., above that of the melting point of the highest melting lower melting-point fat and wherein the lower melting-point fats are present at a level of greater than 50 wt. % of the total lipid in the lipid phase, for example greater than 60 wt. %, for example greater than 70 wt. %, for example greater than 90 wt. %.

Solid particles having a particle size of less than 500 μm, for example less than 180 μm, may be added to the composition comprising triglycerides in the process of the invention. The solid particles may have a D90 particle size of less than 100 μm, for example less than 50 μm, for example less than 30 μm. The solid particles may be added before the composition forms a gel. The solid particles added to the composition comprising triglycerides may be selected from the group consisting of modified starch, maltodextrin, inorganic salt, protein particles, fibres, plant particles, sugars, hydrogel particles and combinations of these. The solid particles may have been ground or aggregated. The solid particles added to the composition comprising triglycerides may be maltodextrin. The solid particles may be present at a level of between 1 and 20% of the total lipid weight in the foam.

Cooling the triglyceride composition will promote the formation of crystals. This can be enhanced by the addition of small crystals, for example crystals of a higher melting fat. The added crystals may themselves occupy the surface of the gas bubbles when the gel is aerated, or they may promote the growth of crystals which occupy the surface of the gas bubbles or a mixture of both. Accordingly, triglyceride crystals may be added to the composition comprising triglycerides in the process of the invention, for example they may be added whilst controlling the temperature of the lipid composition.

The composition comprising triglycerides may initially be at a temperature at which it contains less than 0.1 wt. % solid lipid in the process of the invention. For example it may be at a temperature at which it contains no solid lipid. Starting with less than 0.1 wt. % solid lipid, or no solid lipid, makes it easier to control the conditions such that a proportion of the composition comprising triglycerides crystallizes, providing suitable crystals for occupying the surface of gas bubbles in the foam generated by the process of the invention.

The inventors have found that improved results (e.g. lower density foams and greater stability) may be obtained if the gel is allowed to mature before being aerated. There may be a time interval of at least 5 minutes between the formation of the gel and the start of the aeration in the process of the invention. The time interval between the formation of the gel and the start of the aeration in the process of the invention may be at least 30 minutes, for example at least 1 hour, for example at least 24 hours, for example at least 4 weeks. At long maturation times, the stability of the foam increases with maturation time but the density starts to decrease. The time interval between the formation of the gel and the start of the aeration in the process of the invention may be between 1 hour and 2 weeks, for example between 1 hour and 1 week, for further example between 1 hour and 24 hours. The gel may be maintained at any temperature during the time between formation of the gel and the start of the aeration as long as the composition maintains a solid lipid content between 0.1 and 80%. The inventors have found that the higher the temperature of the gel when it is whipped, the lower the density of foam obtained, providing the temperature is not raised to the point that all triglyceride crystals melt and the gel is destroyed. For example, the composition comprising triglycerides may be cooled rapidly, such as in a freezer at −18° C. to form a gel, and then allowed to warm up to a temperature at which only a few percent solid lipid remains before being aerated.

The aeration step in the process of the invention may comprise mechanical agitation, for example whipping. The inventors have found that although foams could be obtained by non-mechanical agitation methods, such as dissolving or dispersing gas under pressure and then releasing it, to obtain the most stable foams it was preferable to apply mechanical agitation. Without wishing to be constrained by theory, the inventors believe that mechanical agitation increases the wrapping of the gas bubbles with triglyceride crystals. Mechanical agitation may for example be applied using rotor-stator type of equipment, such as a Haas-Mondomix aerating system. After formation, and maturation (if any), the gel may be gently sheared to allow an easy transfer to the aerating system. Mechanical agitation, for example whipping, may be applied for at least 5 s (such as the residence times in a continuous rotor-stator system), for example at least 1 minute, for example at least 5 minutes (such as in a batch whipping machine), for example at least 10 minutes, for further example at least 30 minutes. Foam stability generally increases with increasing mechanical agitation time. In contrast to many foams, the foam generated according to the process of the invention is not particularly sensitive to over-whipping. The aeration step in the process of the invention may comprise gas depressurization followed by mechanical whipping. Such a combination of initial bubble generation using dissolved/dispersed gas and a pressure drop followed by mechanical agitation may usefully be employed, however all process steps may be performed at or near atmospheric pressure, for example at an absolute pressure of between 800 hPa and 2100 hPa, for example between 850 hPa and 1100 hPa.

The process of the invention may further comprise adding additional materials. For example the process may include adding additional food ingredients and forming a food product. The process may include adding additional materials before the formation of the gel, after a gel is formed or to the foam.

The foam obtained in the process of the invention by aerating the gel may be mixed with un-aerated composition, for example the foam may be mixed with an un-aerated composition having a lipid continuous phase. Such a "two-step" process is particularly effective at creating an aerated composition having a low lipid content when the foam obtained in the process of the invention has a lipid content higher than the un-aerated composition. Lipid-continuous compositions with low lipid contents are difficult to aerate, as the foam structure tends to break during whipping. The inventors were surprised to find that by creating a foam according to the process of the invention using a composition with a high lipid content and then carefully mixing the foam with an un-aerated material with a lower fat content they could obtain much higher porosity than could be obtained by whipping the final composition directly. Without wishing to be bound by theory, the inventors believe that the formation of crystal-wrapped bubbles in the initial foam provides a foam with good stability during mixing, allowing it to be mixed into un-aerated material with very little loss of porosity.

In an embodiment of the process of the invention, the lipid phase of the composition comprising triglycerides may have at least 80% of its total crystallization enthalpy between 80° C. and −20° C. occurring in a temperature range of at least 20° C., for example a range of at least 30° C. In an embodiment of the process of the invention the lipid phase of the composition of the invention may have at least 50% of its total crystallization enthalpy between 80° C. and −20° C. occurring in a temperature range between 40° C. and 15° C., for example at least 80% of its total crystallization enthalpy between 80° C. and −20° C. occurring in a temperature range between 40° C. and 15° C. In a further embodiment of the process of the invention the lipid phase of the composition of the invention may have at least 50% of its total crystallization enthalpy between 80° C. and −20° C. occurring in a temperature range between 20° C. and −5° C., for example at least 80% of its total crystallization enthalpy between 80° C. and −20° C. occurring in a temperature range between 20° C. and −5° C.

The process of the invention may comprise the steps of providing a composition comprising triglycerides and having a lipid content greater than 40 wt. %; controlling the temperature of the composition such that the composition comprises triglyceride crystals, has a solid lipid content between 0.1 and 80% (for example between 0.1 and 60%, for example between 0.5 and 40%, for example between 1 and 20%, for example between 5 and 20%), and forms a gel; aerating the gel to form a foam; and mixing the foam with an un-aerated lipid-continuous composition having a lipid content lower than 40 wt. % to form a further foam. The further foam formed by mixing the initial foam with an un-aerated lipid-continuous composition may have a lipid content below 40 wt. %, for example below 35 wt. %, for further example below 30 wt. %. The foams may comprise gas bubbles having their surface occupied by crystals comprising triglycerides. In the context of the present invention, the term "un-aerated" refers to a composition having a porosity below 1%, for example the un-aerated lipid-continuous composition may have a porosity in the lipid phase of less than 1%.

The temperature of the composition comprising triglycerides may be controlled to form a gel, for example by rapid cooling, and then further ingredients mixed in, acting to increase the temperature of the gel ready for efficient aeration, but without melting out all the solid lipid content. It is an advantage of the process of the invention that it provides a foam with good stability such that additional ingredients may be mixed into the foam without leading to too great an increase in density. The foam may be allowed to mature before additional ingredients are added. For example the time interval between the formation of the foam and the addition of further ingredients, for example food ingredients, may be at least 30 minutes, for example at least 1 hour, for example at least 24 hours, for example at least 4 weeks.

In an embodiment of the process of the invention, the process may comprise the steps of providing a composition comprising triglycerides having a cocoa butter content between 5 and 50% by weight (for example between 15 and 25% by weight) and a lower melting-point fat content between 50 and 95% by weight (for example between 85 and 50% by weight), wherein the lower melting-point fat has a highest melting point below 0° C. (for example below −10° C.); cooling the composition to a temperature between 0 and 15° C. such that the composition comprises triglyceride crystals, has a solid lipid content between 0.1 and 80% (for example between 5 and 20%) and forms a gel; and aerating the gel (for example by mechanical whipping) to form a foam. The composition comprising triglycerides may be free from lipid crystals before being cooled. The resulting foam may optionally be mixed with an un-aerated lipid-continuous composition.

In a further embodiment of the process of invention, the process may comprise the steps of providing a composition comprising triglycerides having a higher melting-point fat content between 5 and 50% by weight (for example between 15 and 25% by weight) and a lower melting-point fat content between 50 and 95% by weight (for example between 50 and 85% by weight), wherein the higher melting-point fat has a lowest melting point above 30° C. (for example above 35° C., for further example above 40° C.) and the lower melting-point fat has a highest melting point below 10° C. (for example below 0° C., for further example below −10° C.); cooling the composition to a temperature between 0 and 25° C. (for example between 0 and 15° C.) such that the composition comprises triglyceride crystals, has a solid lipid content between 0.1 and 80% (for example between 5 and 20%) and forms a gel; and aerating the gel (for example by mechanical whipping) to form a foam. The composition comprising triglycerides may be free from lipid crystals before being cooled. The resulting foam may optionally be mixed with an un-aerated lipid-continuous composition.

Those skilled in the art will understand that they can freely combine all features of the present invention disclosed herein. In particular, features described for the product of the present invention may be combined with the process of the present invention and vice versa. Further, features described for different embodiments of the present invention may be combined. Where known equivalents exist to specific features, such equivalents are incorporated as if specifically referred to in this specification. Further advantages and features of the present invention are apparent from the figures and non-limiting examples.

EXAMPLES

Example 1

Formation of Stable Foams with Cocoa Butter in High Oleic Sunflower Oil

High Oleic Sunflower Oil (HOSFO) having a melting point of −17° C. (±3)° C. was obtained from (SABO Nestrade). Cocoa butter (Pure Prime Pressed) having a melting point of 35° C. (±3)° C. was obtained from Cargill.

The melting and crystallizing profile of 20 wt. % cocoa butter in HOSFO was measured by DSC using a SDT Q600 from TA instruments. A sample of around 10-20 mg of cocoa butter in HOSFO was heated to 70° C. before recording the crystallization signature. After cooling to −20° C., it was reheated to 70° C. to record the melting signature. The DSC trace is shown in FIG. 1. It can be seen that the highest melting peak has a peak maximum at about 23° C. and the peak starts at around 17° C. Although different lipids and crystalline forms may have slightly different specific melting enthalpies, the area under the melting peaks in the reheating trace provides a reasonable correlation with the quantity of lipid melting. From the DSC reheating trace it can be seen that by 5° C. less than 60% of the lipid remains solid.

Figure 2:
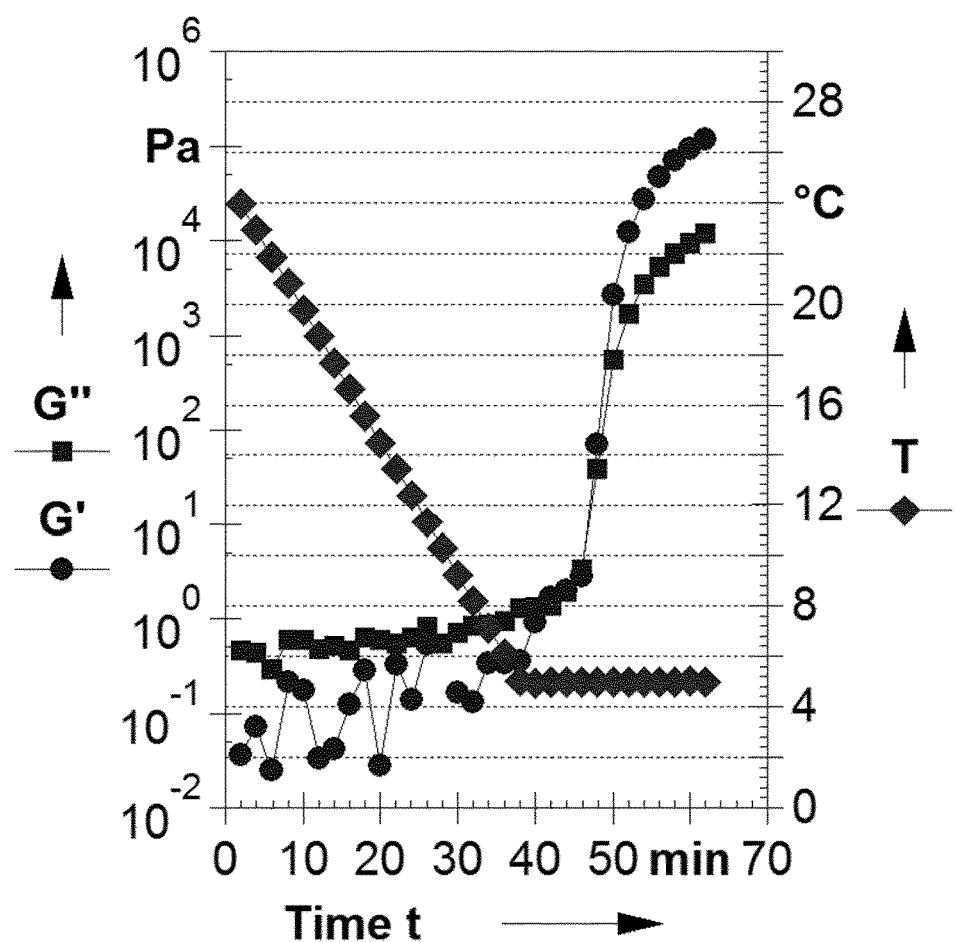
FIG. 2 shows the evolution of rheological properties during gelation as cooling is applied from fully melted state down to 5° C., for 20% cocoa butter in HOSFO.

The formation of a gel was confirmed. FIG. 2 shows the evolution of G' (●) and G" (■) with time (sec), recorded at 1 Hz, for 20% cocoa butter (PPP) in HOSFO cooling down from 25° C. to 5° C. (♦) and stabilizing at 5° C., with a cooling rate of 0.5° C./min. The strain amplitude was kept at 0.005% to ensure to be in the linear deformation regime. Geometry used was concentric cylinders. Gelation profile of 20% cocoa butter in HOSFO as temperature was lowered from 25° C. to 5° C. The mixture was initially heated up to 70° C. for achieving complete dissolution, then the temperature was lowered to 25° C. within ½ hour prior to recording rheological data during gelation. It can be seen that after 45 minutes when the gel forms, G' is greater than G" and G' is greater than 10 Pa.

1.1 Gel at 4° C., Whipping at 20° C.

Mix preparation: 20% (w/w) cocoa butter in HOSFO was heated to 70° C. until complete dissolution. 250 g of the heated solution was placed in a double-jacketed glass container. The mixture was cooled down over 20 hours by applying water at 4° C. to the jacket. The gel obtained was placed at 20° C. in a Hobart N50 planetary kitchen mixer fitted with a balloon whisk at speed 2 for 15, 30, 45 min. A foam with an overrun of 240% was obtained. (Overrun is the volume of gas incorporated into the foamed material/volume of the un-foamed material, expressed in %.) The bubble size distribution was wide, with an average size estimated in the range 0.02-0.05 mm, but with only a very small fraction (less than 5%) of bubbles larger than 0.1 mm. The foam had good stability at low temperatures, but if maintained at room temperature it collapsed over 1 hour.

1.2 Gel at 4° C., Whipping at 5° C.

Figure 3:
FIG. 3 shows a 20 wt. % cocoa butter in high oleic sunflower oil foam, prepared as described in example 1, trial 1.2, after 7 days of storage.

The protocol was same as 1.1 above except that whipping was performed at 5° C. by placing the kitchen mixer in a cold room. A high overrun foam was achieved (200% after 15 minutes whipping). Bubble size distribution was wide, with an average size estimated in the range 0.03-0.05 mm, but with only a very small fraction (less than 5%) of bubbles larger than 0.1 mm. The foam had good stability at low temperatures, but if maintained at room temperature after foaming, the foam showed around 1 cm of drainage after 7 days of storage at room temperature (see FIG. 3). The texture of the foam was much firmer and less prone to flow than that of the gel before whipping.

1.3 Gel Held at 5° C. for 1 Week—Foaming at 5° C.

Figure 4:
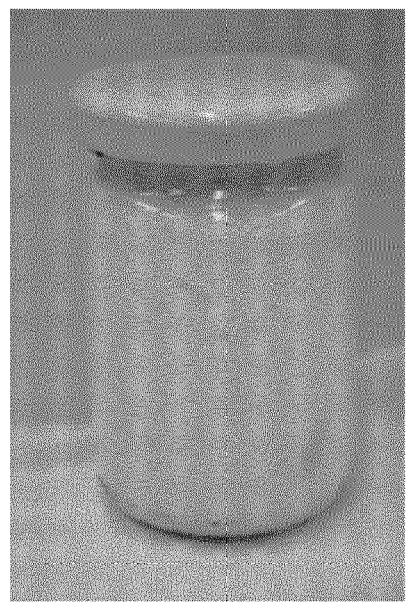
FIG. 4 shows a 20 wt. % cocoa butter in high oleic sunflower oil foam, prepared as described in example 1, trial 1.3, after 7 days of storage.

The protocol was the same as 1.1 above, except that 250 g of the mix was stored at 5° C. for 1 week, which allowed for recrystallization. The gel was then whipped at 5° C. for 15 min, 30 min and 45 min. A high overrun foam was achieved (180% after 15 minutes whipping and 235% after 30 minutes whipping). Average bubble size was smaller than in the earlier trials, estimated to be 0.03-0.05 mm, leading to very white appearance of foam. Foam showed a better stability at room temperature, i.e. it could be stored for weeks without apparent macroscopic collapse, and with very limited drainage (below 1 mm of drainage after 7 days of storage) (see FIG. 4).

1.4 Gel Held at 5° C. for 1 Week—Foaming at 20° C.

The protocol was the same as in 1.3 above except that whipping was performed at 20° C. A high overrun foam was achieved (225% after 15 minutes). Stability and bubble size was similar to 1.3.

1.5. Gel Held at 5° C. for 2 Weeks—Foaming at 5° C.

The protocol was same as in 1.3 except the gel storage duration which was 2 weeks. The stability and bubble size was similar to 1.3.

Summary of results foaming 20% cocoa butter in high oleic sunflower oil:

| Conditions | Max overrun |
|---|---|
| Gel 4° C. - Foamed at 20° C. | 243% |
| Gel 4° C. - Foamed at 5° C. | 245% |
| Gel held at 5° C. for 1 week. Foamed at 5° C. | 235% |
| Gel held at 5° C. for 2 weeks. Foamed at 5° C. | 200% |
| Gel held at 5° C. for 1 week. Foamed at room temperature | 226% |

Example 2

Foams with Cocoa Butter in High Oleic Sunflower Oil with Addition of Maltodextrin Particles Mix preparation: 20 wt. % cocoa butter, 10 wt. % maltodextrin particles (DE11-14) in HOSFO was heated to 70° C. until complete dissolution of the cocoa butter. 250 g of the mix placed in a closed vial. The vial was placed in water, cooled within a double-jacketed container (cooling water at 4° C.) for 20 hours. The gel obtained was stored at 5° C. for 1 week before being placed in a Hobart kitchen mixer at 5° C. fitted with a balloon whisk and whipped at speed 2 for 15 min, 30 min and 45 min. The resulting foam was compared with trial 1.3 above which had the same conditions apart from no maltodextrin particles. The foam with maltodextrin particles has a maximum overrun of 214% (compared to 235% for the sample with no particles). However, the trial with maltodextrin had improved stability against coarsening over time and showed better homogeneity of the foam.

Example 3

Foaming of Other Fats at 20 wt. % in High Oleic Sunflower Oil

A series of other fats were prepared at 20 wt. % in high oleic sunflower oil, being completely melted and then cooled to a gel. The samples were whipped as in example 1.

| Fat | Conditions | Max overrun & comments |
| --- | --- | --- |
| Refined hydrogenated coconut oil, Mpt. 38° C. (Peerless Foods, Australia) | Gel stored at 15° C. for 15 h, then at 5° C. for 1 h. Whipped at 5° C. | 187% Poor storage at 20° C., but good at 5° C. |
| Hydrogenated palm kernel oil, Mpt. 45° C. (Lam Soon, Thailand) | Gel stored at 15° C. for 15 h, then at 5° C. for 2 h. Whipped at 5° C. | 177% Stable at 20° C. without drainage after 7 days but with some contraction |
| Cocoa Butter equivalent, Mpt. 45° C. (Loders Croklaan) | Gel stored at 15° C. for 15 h, then at 5° C. for 20 h. Whipped at 5° C. | 264% Stable at 20° C. without drainage after 7 days |
| High melting palm fraction, Mpt. 60° C. (AAK Sweden) | Gel stored at 20° C. for 16 h, then at 5° C. for 1 h. Whipped at 5° C. | 141% Stable at 20° C. without drainage after 7 days |
| Interesterified cocoa butter, Mpt. 52° C. (Cargill) | Gel stored at 5° C. for 5 h, then at 5° C. for 1 h. Whipped at 5° C. | 75% 1 cm drainage after 7 days at 20° C. |

Example 4

Foaming of Single Oil

High stearic sunflower oil stearin (Nutrisun) is a high melting fraction of sunflower oil. Melting point 32° C. (±3° C.).

The high stearic sunflower oil stearin was heated to 90° C. to ensure complete dissolution of crystals. 250 g of the heated solution was placed in a double-jacketed glass container. The mixture was cooled down over 20 hours by applying water at 20° C. to the jacket. The gel obtained was placed in a Hobart kitchen mixer fitted with a balloon whisk at speed 2 for 15 min. High overrun foam was made (max overrun=277% after 45 min whipping). This foam showed good heat stability without apparent macroscopic destabilization and without apparent drainage after 7 days of storage.

Bubble size distribution was very wide, with an average size estimated in the range 0.06-0.08 mm, but with only a very small fraction (less than 5%) of bubbles larger than 0.1 mm. This demonstrates that foams may be produced from single fats (for example vegetable fats from a single plant source), the crystals occupying the surface of the gas bubbles necessarily coming from the same fat.

Example 5

Bubbles Coated by Crystals

Figure 5:
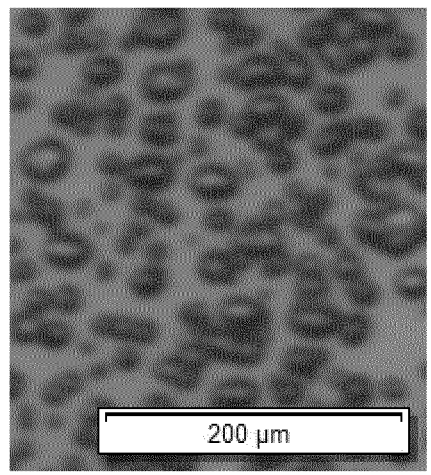
FIG. 5 is a micrograph of 20 wt. % cocoa butter in high oleic sunflower oil foam, prepared as described in example 1, trial 1.5, showing the absence of shape relaxation in the dense layer of crystals adsorbed at the surface of the bubbles.
Figure 6:
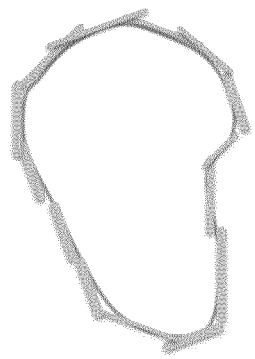
FIG. 6 is a schematic illustration of the absence of shape relaxation around a bubble.

FIG. 5 shows the dense layer of crystals absorbed at the surface of bubbles in a micrograph of the cocoa butter/high oleic sunflower oil foam formed in trial 1.5 above. The image illustrates the type of non-spherical shapes that are found under the microscope, whereby interfacial stabilization by surface adsorption of a dense layer of crystals creates the property of the non-relaxing shape (shown diagrammatically in FIG. 6). By diluting the foam with liquid oil (e.g. the same liquid oil used for foaming) the bulk rheological effects normally acting on bubble shape are suppressed, but the interfacial stabilization of the crystals around the bubbles can be observed by the fact that the bubble shapes do not relax. From microscopical observations of these foams, around 50% of bubbles were found to have a surface coverage of at least 50% of the maximal surface coverage. Maximal surface coverage corresponds to a jammed structure of crystals adsorbed at a bubble's interface, or at the interface between two bubbles. The dense packing of crystals at bubble interfaces gives good stability.

Figure 7:
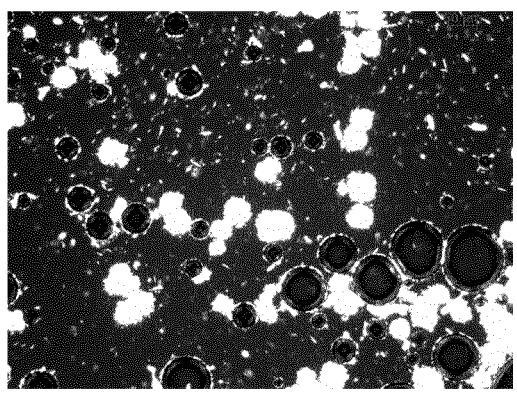
FIG. 7 is a polarized optical micrograph of a foam of 20 wt. % high melting palm fraction in high oleic sunflower oil.
Figure 8:
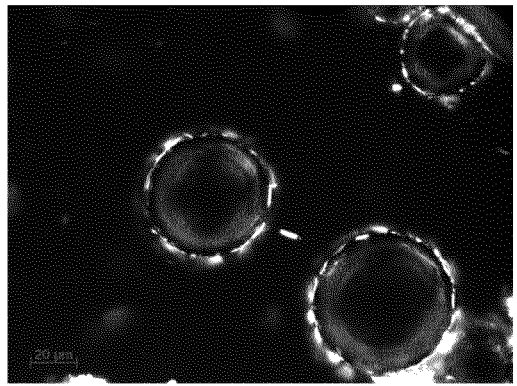
FIG. 8 is a polarized optical micrograph of a foam of 20 wt. % high melting palm fraction in high oleic sunflower oil, diluted by a factor of around 5.

A high melting palm oil fraction (AAK, Sweden) was foamed in HOSFO and the structure studied by microscopy. Mix preparation: 20% high melting palm oil fraction was dissolved in HOSFO by heating to 75° C. A gel formed during storage at 20° C. for 16 h. 250 g of the gel obtained was placed in a Hobart kitchen mixer and whipped at speed 2 for 45 minutes. FIG. 7 shows a polarized micrograph of the foam not diluted, and then FIG. 8 shows the foam diluted by a factor of around 5 with HOSFO. The micrographs show triglyceride crystals coating the interfaces between bubbles.

Example 6

Foams Stabilized by Triglyceride Crystals—Visualization of the Adsorbed Triglyceride Crystals at Interface by Optical Microscopy HOSFO and 10 wt % cocoa butter improver (CBI) were mixed at 60° C. until complete dissolution. The CBI (Illexao HS90-AAK) is based on fractionated shea butter and has a melting point of 43° C.±3° C. The HOSFO/CBI mixture was removed from the hot plate and left to cool overnight at 5° C. The mixture formed a gel with a paste-like consistency. Foam was generated in a Hobart mixer with balloon whisk, speed 2, for 20 min at 5° C. During whipping, air is incorporated into the gel matrix and forms bubbles coated by crystals that ensure long-term mechanical stability to the foam.

Figure 9:
FIG. 9 is a micrograph of a foam consisting of high oleic sunflower oil and cocoa butter improver
Figure 10:
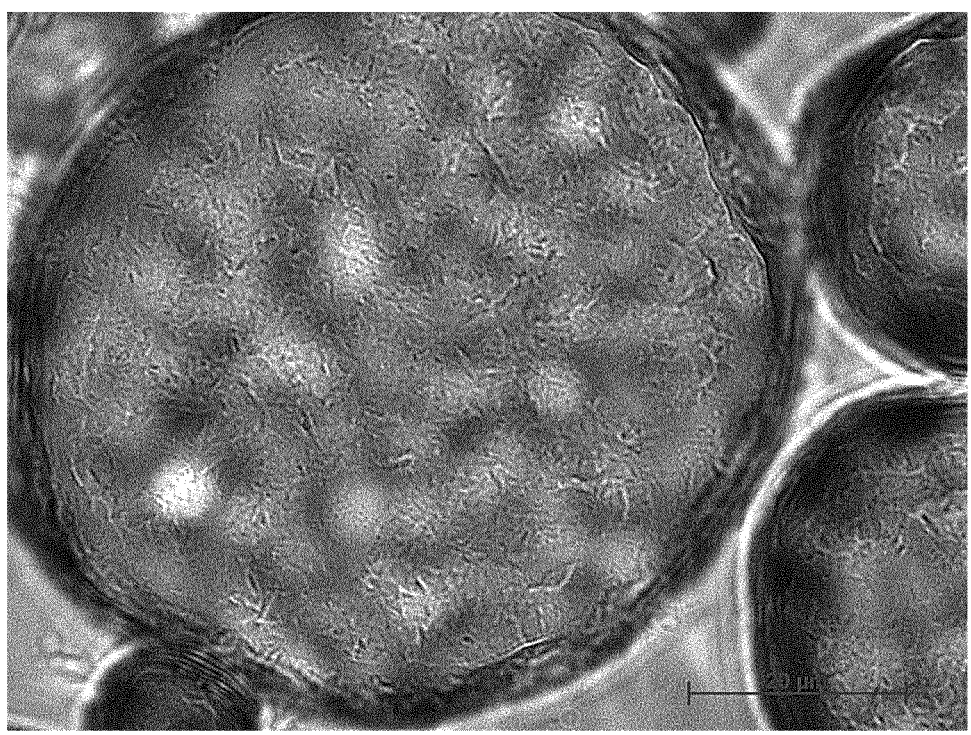
FIG. 10 is a further micrograph of the foam shown in FIG. 9

The samples were examined using optical microscopy. A few drops of the aerated material was placed onto a glass slide and then imaged using appropriate magnification and brightfield illumination using a Zeiss optical microscope. The images (FIGS. 9 and 10) clearly show a complete layer of crystals adsorbed at the air/oil interface and forming a crust wrapping the bubbles. With such a high level of surface coverage it is immediately obvious after inspection by microscopy that at least 50% of the surface of the gas bubbles is occupied by crystals.

Example 7

Forming a Milk-Chocolate Based Foam—1-Step Versus 2-Step Process

An aerated milk chocolate was formed using three different glyceride materials to stabilize the oil foam: a CBI as in example 18, a CBE as in example 3 and monoglycerides as in example 6. For the CBI and monoglycerides, a 1-step process was compared with a 2-step process.

Foaming in 1 Step:

10% glyceride material (CBI or monoglycerides) was mixed with 90% oil (high oleic sunflower oil, HOSFO) and heated until no solids remained. This oil mixture was cooled to 20° C. in a water bath, and maintained at that temperature. The oil mixture formed a gel.

A milk chocolate with 34% fat was fully melted and then cooled down to 30° C. The chocolate was tempered by seeding; 0.2% of Chocoseed A (Fuji) was gently mixed in, ensuring no incorporation of air.

The oil mixture (20%) was combined with the chocolate (80%) and whipped in a Hobart mixer, the temperature being maintained at 30° C. The overrun increased up to a whipping time of 1 hour.

Foaming in 2 Steps:

10% glyceride material (CBI, CBE or monoglycerides) was mixed with 90% oil (HOSFO) and heated until no solids remained. This oil mixture was cooled to 20° C. in a water bath, and maintained at that temperature. The oil mixture formed a gel.

A milk chocolate with 34% fat was fully melted and then cooled down to 30° C. The chocolate was tempered by seeding; 0.2% of Chocoseed A (Fuji) was gently mixed in, ensuring no incorporation of air.

The oil mixture was whipped at 20° C. in a Hobart mixer to form a white foam. The white foam was then gently mixed into the chocolate with a spatula.

The porosities for the aerated milk chocolates obtained are shown below.

| Glyceride used | 1-step | 2-step |
| --- | --- | --- |
| Monoglycerides | 0.16 | 0.26 |
| CBI | 0.30 | 0.38 |
| CBE | — | 0.37 |

Figure 11:
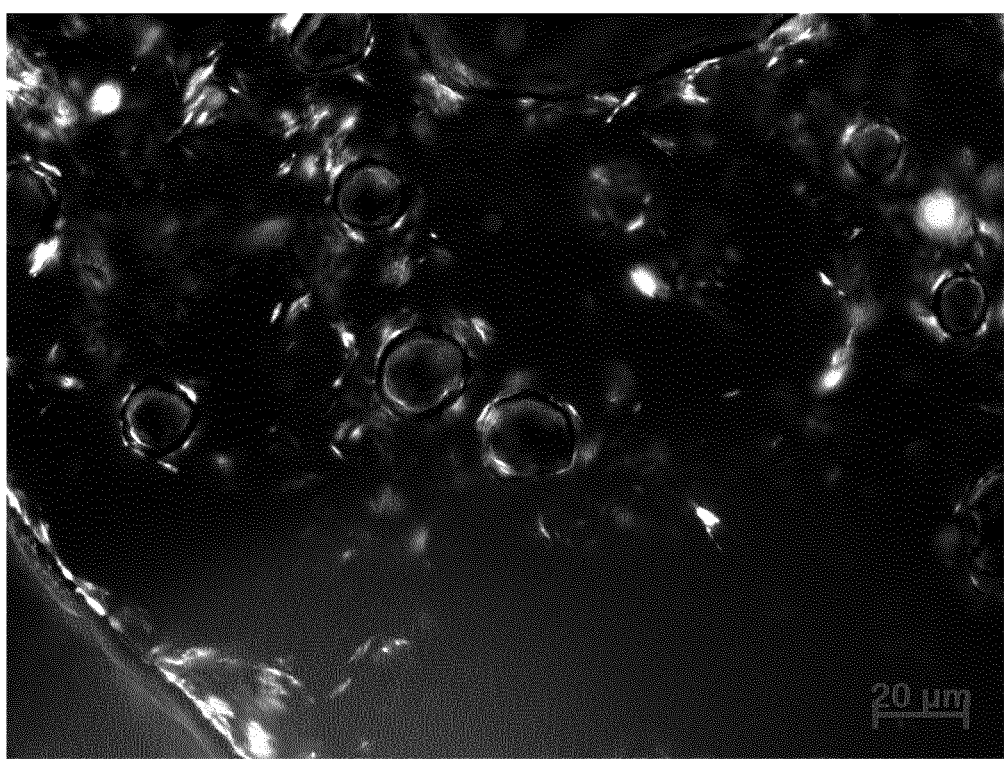
FIG. 11 is a polarized optical micrograph of a foam containing high oleic sunflower oil and cocoa butter equivalent

The 2-step process, where an aerated gel is mixed with an un-aerated composition, resulted in higher porosities. Crystals surrounding the air bubbles could be observed in all samples by microscopy, for example FIG. 11 which shows the CBE oil foam.

The foams obtained using monoglycerides were examined after 20 days storage. The 1-step foam was found to be darker in colour (indicating a lower air content) and, when disturbed, the 1-step foam collapsed more readily. Microscopical observations of the two foams showed that only a few gas bubbles remained in the 1-step foam, and these were mostly large bubbles. The 2-step foam in contrast had a much greater number of bubbles, the bubbles being smaller in size.

Example 8

Biscuit Recipe

A biscuit was prepared using an oil foam to partially replace the fat in the biscuit dough. The reference biscuit was prepared from 140 g melted milk butter, 140 g white, 110 g brown sugar, 1 egg, 1 teaspoon of vanilla extract, 240 g of flour, 6 g of chemical yeast, 6 g of $Na_2CO_3$, 80 g of nuts, 200 g of chocolate (broken into small pieces). All ingredients were mixed together into a dough with the melted butter being added last. The dough was split into 5-10 cm diameter balls and baked for 15 min. at 75° C.

The oil foam biscuit was prepared in a similar manner, but 50% of the butter by volume was replaced by an oil foam. This led to approximately 70 g of butter being replaced by 20 g of the oil foam. The foam was prepared as follows: 10 wt. % of cocoa butter improver (Illexao HS90-AAK), was mixed with HOSFO and warmed until no solid remained. The mixture was placed at 4° C. until it formed a gel (approx. 5 hours) and the gel was then whipped (also at 4° C.) for 1 hour using a kitchen mixer (Hobart, Switzerland) equipped with a balloon whisk. The foam was very stable at 4° C. with no drainage observed. The overrun was between 240-260 vol %, the porosity was therefore between 70 and 72. The oil foam was gently mixed into the other dough ingredients before the melted butter.

Further oil foam biscuits were prepared in the same way but with a cocoa butter equivalent (Coberine®-IOI Loders Croklaan) instead of the cocoa butter improver.

The reference and the oil foam recipes produced acceptable biscuits, with the oil foam biscuits containing less fat by volume.

Example 9

Cake Recipe

A sponge cake was prepared using an oil foam to partially replace the fat in the cake batter. The reference cake was prepared from 500 g egg whites, 350 g caster sugar, 350 g flour, the zest and juice of a lemon and 100 g butter. The egg whites were whipped together with the sugar to obtain a firm foam. The flour was then sifted over the egg mixture and gently folded together before adding the lemon. Finally, the melted butter was folded into the mixture to form a cake batter. The batter was placed in a baking tin and baked at 180° C. for 45 minutes. For the oil foam version, an oil foam was prepared as in example 21. 50% of the butter by volume was replaced by the oil foam in the recipe. This led to 50 g of butter being replaced by approximately 29 g of the oil foam. The oil foam was gently mixed into the other cake ingredients before the melted butter.

Further oil foam cakes were prepared in the same way but with a cocoa butter equivalent (Coberine®-IOI Loders Croklaan) instead of the cocoa butter improver.

The reference and the oil foam recipes produced acceptable cakes. In technical tasting the reference cake and the oil foam versions were found to be very similar.

The invention claimed is:

1. A process for forming a foam, the process comprising:
   providing a composition comprising triglycerides and having a lipid content greater than 20 wt. %, wherein the triglycerides are more than 95 wt. % of the total lipids of the foam, and all fatty acids in the triglycerides have a carbon chain length less than 22;
   cooling the composition to a temperature between 0° C. and 15° C. such that the composition comprises triglyceride crystals, has a solid lipid content between 5% and 20% and forms a gel having a linear shear elastic modulus G' of $10^2$-$10^7$ Pa at 1 Hz; and
   aerating the gel to form a foam comprising bubbles, and the foam does not have a rigid network of crystals between the bubbles, wherein the aerating of the gel comprises mechanical agitation, and the foam contains less than 5 wt. % of water.

2. The process according to claim 1, further comprising adding solid particles having a particle size of less than 500 µm to the composition comprising triglycerides.

3. The process according to claim 1, wherein triglyceride crystals are added to the composition comprising triglycerides.

4. The process according to claim 1, wherein the composition comprising triglycerides is initially at a temperature at which the composition comprising triglycerides contains less than 0.1% solid lipid.

5. The process according to claim 1, wherein there is a time interval of at least 5 minutes between the formation of the gel and the start of the aeration.

6. The process according to claim 1, wherein the aeration comprises gas depressurization followed by mechanical whipping.

7. The process according to claim 1, further comprising adding additional food ingredients to the foam and forming a food product.

8. The process according to claim 1, wherein the foam comprises gas bubbles having at least 50% of their surface occupied by crystals comprising triglycerides.

9. The process according to claim 8, wherein the crystals comprising triglycerides occupying the surface of the gas bubbles form layers having an average thickness below 5 µm.

10. The process according to claim 1, wherein the foam has a continuous lipid phase and a porosity between 1 and 80%.

11. The process according to claim 10, wherein the lipid phase comprises one or more higher melting-point fats and one or more lower melting-point fats and wherein the lowest melting-point of the higher melting-point fats is at least 10° C. above that of the highest melting point of the lower melting-point fats, and wherein the lower melting-point fats are present at a level of greater than 50 wt. % of the total lipids in the lipid phase.

12. The process according to claim 11, wherein the one or more higher melting-point fats are selected from the group consisting of cocoa butter, shea butter, illipe butter, sal fat, kokum butter, mango kernel fat, palm kernel oil, palm oil, coconut oil, milk fat, high stearic sunflower oil and hydrogenation products, inter-esterification products and combinations thereof and the one or more lower melting-point fats are selected from the group consisting of sunflower oil, safflower oil, rapeseed oil, olive oil and combinations thereof.

13. The process according to claim 2, wherein the solid particles are selected from the group consisting of modified starch, maltodextrin, inorganic salt, protein particles, fibres, plant particles, sugars, hydrogel particles and combinations thereof.

\* \* \* \* \*